(12) United States Patent
Hossainy et al.

(10) Patent No.: US 9,327,062 B2
(45) Date of Patent: May 3, 2016

(54) SOLUBLE IMPLANTABLE DEVICE COMPRISING POLYELECTROLYTE WITH HYDROPHOBIC COUNTERIONS

(71) Applicant: Abbott Cardiovascular Systems Inc., Santa Clara, CA (US)

(72) Inventors: Syed F. A. Hossainy, Hayward, CA (US); O. Mikael Trollsas, San Jose, CA (US); Lothar W. Kleiner, Los Altos, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 14/624,063

(22) Filed: Feb. 17, 2015

(65) Prior Publication Data

US 2015/0157771 A1   Jun. 11, 2015

Related U.S. Application Data

(63) Continuation of application No. 13/544,749, filed on Jul. 9, 2012, now Pat. No. 8,986,728, which is a continuation of application No. 12/130,942, filed on May 30, 2008, now abandoned.

(51) Int. Cl.
| | |
|---|---|
| *A61L 31/14* | (2006.01) |
| *A61L 31/06* | (2006.01) |
| *A61L 31/16* | (2006.01) |
| *A61L 31/04* | (2006.01) |
| *A61L 27/34* | (2006.01) |
| *A61L 31/10* | (2006.01) |
| *A61L 27/58* | (2006.01) |
| *A61L 29/14* | (2006.01) |
| *A61L 29/08* | (2006.01) |
| *A61F 2/82* | (2013.01) |
| *C09D 105/08* | (2006.01) |
| *C09D 189/00* | (2006.01) |
| *C09D 101/28* | (2006.01) |
| *C08L 1/28* | (2006.01) |
| *C08L 5/08* | (2006.01) |
| *C08L 89/00* | (2006.01) |

(52) U.S. Cl.
CPC .............. *A61L 31/148* (2013.01); *A61L 27/34* (2013.01); *A61L 27/58* (2013.01); *A61L 29/085* (2013.01); *A61L 29/148* (2013.01); *A61L 31/048* (2013.01); *A61L 31/06* (2013.01); *A61L 31/10* (2013.01); *A61L 31/16* (2013.01); *C08L 1/286* (2013.01); *C08L 5/08* (2013.01); *C08L 89/00* (2013.01); *C09D 101/286* (2013.01); *C09D 105/08* (2013.01); *C09D 189/00* (2013.01); *A61F 2/82* (2013.01); *A61L 2300/602* (2013.01)

(58) Field of Classification Search
None
See application file for complete search history.

(56) References Cited

U.S. PATENT DOCUMENTS

| | | |
|---|---|---|
| 3,072,618 A | 1/1963 | Turbak |
| 3,665,054 A | 5/1972 | Burrows et al. |
| 4,083,893 A | 4/1978 | Lofquist et al. |
| 4,179,497 A | 12/1979 | Cohen et al. |
| 4,837,015 A | 6/1989 | Olsen |
| 4,879,135 A | 11/1989 | Greco et al. |
| 4,895,566 A | 1/1990 | Lee |
| 5,419,847 A | 5/1995 | Showell et al. |
| 5,420,197 A | 5/1995 | Lorenz et al. |
| 5,476,909 A | 12/1995 | Kim et al. |
| 5,686,147 A | 11/1997 | Ngoc |
| 5,753,264 A | 5/1998 | Magdassi et al. |
| 5,840,387 A | 11/1998 | Berlowitz-Tarrant et al. |
| 5,874,100 A | 2/1999 | Mahoney et al. |
| 5,993,972 A | 11/1999 | Reich et al. |
| 6,398,758 B1 | 6/2002 | Jacobsen et al. |
| 6,455,547 B1 | 9/2002 | Kis |
| 6,525,145 B2 | 2/2003 | Gevaert et al. |
| 6,939,376 B2 | 9/2005 | Shulze et al. |
| 7,033,602 B1 | 4/2006 | Pacetti et al. |
| 7,212,971 B2 | 5/2007 | Jost et al |
| 7,225,518 B2 | 6/2007 | Eidenschink et al. |
| 7,279,174 B2 | 10/2007 | Pacetti et al. |
| 7,284,401 B2 | 10/2007 | Larson et al. |
| 7,314,480 B2 | 1/2008 | Eidenschink et al. |
| 7,544,414 B2 | 6/2009 | Tsutsumi et al. |
| 7,645,504 B1 | 1/2010 | Pacetti |
| 7,758,892 B1 | 7/2010 | Chen et al. |
| 7,794,495 B2 | 9/2010 | Gale et al. |
| 7,939,096 B2 | 5/2011 | Wilson |
| 8,202,529 B2 | 6/2012 | Hossainy et al. |

(Continued)

FOREIGN PATENT DOCUMENTS

| | | | |
|---|---|---|---|
| CN | 101177494 A | 5/2008 | |
| WO | WO 03/092754 | 11/2003 | |
| WO | WO 2004/069169 | 8/2004 | |
| WO | WO 2005/115496 | 8/2005 | |
| WO | WO 2008027989 A2 * | 3/2008 | ............. A61L 27/14 |
| WO | WO 2009/148777 | 12/2009 | |

OTHER PUBLICATIONS

Fitzgerald et al. "Cation-Anion and Cation-Cation Interactions in Sulfonated Polystyrene Ionomers; Spectroscopic Studies of the Effects of Solvents," ACS Symposium Series 302, Eds. A. Eisenbergy and F.E. Bailey, pp. 36-52., American Chemical Society, 1986.

Fitzgerald et al. "Synthesis, Properties, and Structure of Sulfonate Ionomers," JMS-Rev. Macromol. Chem. Phys., 1988, C28(1), pp. 99-185.

(Continued)

*Primary Examiner* — Robert A Wax
*Assistant Examiner* — Caralynne Helm
(74) *Attorney, Agent, or Firm* — Squire Patton Boggs (US) LLP

(57) ABSTRACT

The present invention provides an implantable device having a biosoluble coating comprising a polyelectrolyte and a counterion and the methods of making and using the same.

20 Claims, No Drawings

(56) References Cited

U.S. PATENT DOCUMENTS

| | | |
|---|---|---|
| 8,343,529 B2 | 1/2013 | Hossainy et al. |
| 8,703,169 B1 | 4/2014 | Lee et al. |
| 8,986,728 B2 | 3/2015 | Hossainy et al. |
| 2002/0103526 A1 | 8/2002 | Steinke |
| 2004/0180039 A1 | 9/2004 | Toner et al. |
| 2004/0215306 A1 | 10/2004 | Heil, Jr. et al. |
| 2005/0004661 A1 | 1/2005 | Lewis et al. |
| 2005/0129727 A1 | 6/2005 | Weber et al. |
| 2005/0147647 A1 | 7/2005 | Glauser et al. |
| 2005/0165476 A1 | 7/2005 | Furst et al. |
| 2005/0171596 A1 | 8/2005 | Furst et al. |
| 2005/0181015 A1 | 8/2005 | Zhong |
| 2005/0208100 A1 | 9/2005 | Weber et al. |
| 2005/0232962 A1 | 10/2005 | Vrijhof et al. |
| 2005/0255142 A1 | 11/2005 | Chudzik et al. |
| 2005/0287111 A1 | 12/2005 | Schlenoff et al. |
| 2006/0009839 A1 | 1/2006 | Tan |
| 2006/0122096 A1* | 6/2006 | Rozema .......... A61K 47/48215 530/345 |
| 2006/0160985 A1 | 7/2006 | Pacetti et al. |
| 2006/0171895 A1 | 8/2006 | Bucay-Couto |
| 2006/0188486 A1 | 8/2006 | Carpenter et al. |
| 2006/0198869 A1 | 9/2006 | Furst et al. |
| 2006/0222681 A1 | 10/2006 | Richard et al. |
| 2007/0003589 A1 | 1/2007 | Astafieva et al. |
| 2007/0077271 A1 | 4/2007 | Dornish et al. |
| 2007/0154513 A1 | 7/2007 | Atanasoska et al. |
| 2007/0224244 A1 | 9/2007 | Weber et al. |
| 2007/0254012 A1 | 11/2007 | Ludwig et al. |
| 2008/0145416 A1 | 6/2008 | Bronich et al. |
| 2008/0223578 A1* | 9/2008 | Berkland .............. C09K 8/512 166/300 |
| 2008/0299198 A1 | 12/2008 | Ho et al. |
| 2009/0110711 A1 | 4/2009 | Trollsas et al. |
| 2009/0297635 A1 | 12/2009 | Sheth |
| 2011/0054347 A1 | 3/2011 | Goss et al. |

OTHER PUBLICATIONS

Lundberg et al. "Solution Behavior of Ionomers. I. Metal Sulfonate Ionomers in Mixed Solvents," Journal of Polymer Socience, 1980, vol. 18, pp. 1821-1836.

Lundberg et al. "Solution Behavior of Metal Sulfonate Ionomers. II. Effects of Solvents," Journal of Polymer Science: Polymer Physics Edition. 1982, vol. 20, pp. 1143-1154.

Lundberg et al. "Solution Behavior of Sulfonate Ionomer Interpolymer Complexes," Journal of Polymer Science: Part B: Polymer Physics, 1989, vol. 27, pp. 245-260.

Peiffer et al. "Solution Properties of Ion-Containing Polymers in Polar Solvents," Journal of Polymer Science: Polymer Chemistry Edition, 1984, vol. 22, pp. 1757-1773.

Sabbagh et al. "Solubility of highly charged anionic polyelectrolytes in presence of multivalent cations: Specific interaction effect," Eur. Phys., J.E 1, 2000, pp. 75-86.

Solis et al. "Flexible linear polyelectrolytes in multivalent salt solutions: Solubility conditions," Eur. Phys. J.E 4, 2001, pp. 143-152.

Weiss et al. "Comparison of Styrene Ionomers Prepared by Sulfonating Polystyrene and Copolymerizing Styrene with Styrene Sulfonate," Journal of Polymer Science: Polymer Chemsitry Edition, 1985, vol. 23, pp. 549-568.

Babu et al. The AAPS Journal 2004 6:1-12.

Borges et al. International Journal of Pharmaceutics 2005, 299:155-166.

Biillesfeld et al., Long-term evaluation of paclitaxel-coated stents for treatment of native coronary lesions. *Z. Kardiol.* (2003) 92:825-832.

Elabd et al. Polymer 2004 45:3037-3043.

Grube et al., Safety and Performance of a Paclitaxel-Eluting Stent for the Treatment of In-Stent Restenosis: Preliminary Results of the Taxus III Trial. *JACC Angiography & Interventional Cardiology* (2002) 1174-15 Abstract:58A-59A.

Grube et al., Six-and Twelve-Month Results from a Randomized, Double-Blind Trial on a Slow-Release Paclitaxel-Eluting Stent for De Novo Coronary Lesions. *Circulation* (2003) 107:38-42.

Harper, Drug Latentiation. *Progress in Drug Research* (1962) 4:221-294.

U.S. Appl. No. 11/899,740, filed Sep. 6, 2007, Hossainy et al.

U.S. Appl. No. 12/130,948, filed May 30, 2008, Hossainy et al.

Huh et al. "PLGA-PEG Block copolymers for Drug Formulations", Issue Date: vol. 3, No. 5 Jul./Aug. 2003, posted on:Mar. 28, 2008, 10 pgs.

Hwang et al., Physiological Transport Forces Govern Drug Distribution for Stent-Based Delivery. *Circulation* (2001) 104:600-605.

International Search Report for PCT/US2009/043650, mailed Aug. 17, 2010, 4 pgs.

Itaya et al. Journal of Polymer Science Part B Polymer Physics 1994 32:171-177.

Kikuchi et al. Journal of Controlled Release, 1999, 58:21-28.

Lambert et al., Localized Arterial Wall Drug Delivery from a Polymer-Coated Removable Metallic Stent. *Circulation* (1994) 90:1003-1011.

Lincoff et al., Sustained Local Delivery of Dexamethasone by a Novel Intravascular Eluting Stent to Prevent Restenosis in the Porcine Coronary Injury Model. (1997) *JACC* 29:808-816.

Marx et al. Circulation 2001 104:852-855.

Miller-Chou et al., A review of polymer dissolution. *Prog. Polym. Sci.* (2003) 28:1223-1270.

Roche, Design of Biopharmaceutical Properties through Prodrugs and Analogs. *Am. Pharma. Assoc. Academy of Pharm. Sciences*, book, 4 title pages.

Sankalia et al., Reversed chitosan-alginate polyelectrolyte complex for stability improvement of alpha-amylase: Optimization and physicochemical characterization. *European Journal of Pharmaceutics and Biopharmaceutics* (2007) 65:215-232.

Sinkula et al., Rationale for Design of Biologically Reversible Drug Derivatives: Prodrugs. *J. of Pharm. Sciences* (1975) 64:181-210.

Stella et al., Prodrugs: Do they have Advantages in Clinical Practice? *Drugs* (1985) 29:455-473.

Tanabe et al., In-Stent Restenosis Treated with Stent-Based Delivery of Paclitaxel Incorporated in a Slow-Release Polymer Formulation. *Circulation* (2003) 107:559-564.

Van der Giessen et al., Marked Inflammatory Sequelae to Implantation of Biodegradable and Nonbiodegradable Polymers in Porcine Coronary Arteries. *Circulation* (1996) 94:1690-1697.

Zhang et al., Natural polyelectrolyte films based on layer-by layer deposition of collagen and hyaluronic Acid. *Biomaterials* (2005) 26:3353-3361.

\* cited by examiner

SOLUBLE IMPLANTABLE DEVICE COMPRISING POLYELECTROLYTE WITH HYDROPHOBIC COUNTERIONS

CROSS-REFERENCE TO RELATED APPLICATIONS

This application is a continuation of U.S. patent application Ser. No. 13/544,749, filed on Jul. 9, 2012, published as United States patent application publication no. US 2012-0276185 A1 on Nov. 1, 2012, and issuing as U.S. Pat. No. 8,986,728 B2 on Mar. 24, 2015, which is a continuation of U.S. patent application Ser. No. 12/130,942, filed on May 30, 2008, and now abandoned; the content of both of which are fully incorporated herein by reference in their entirety.

FIELD OF THE INVENTION

The present invention relates to a medical device having a soluble coating or a soluble body structure.

BACKGROUND OF THE INVENTION

An ongoing goal of biomaterials research is the improvement of compositions from which medical articles, such as medical devices and coatings for medical devices, are produced. An example of such a medical article is an implantable medical device.

In a variety of medical procedures such as, for example, percutaneous transluminal coronary angioplasty (PTCA), stents play an important role. Stents act as a mechanical intervention to physically hold open and, if desired, expand a passageway within a subject. However, thrombosis and restenosis, which may develop several months after a particular procedure, are among the problems associated with the use of stents and can create a need for additional angioplasty or a surgical by-pass operation.

In order to address these problems, stents are being developed to provide for the local delivery of agents. A method of local delivery includes coating the surface of a medical article, e.g., a stent, with a polymeric carrier and attaching an agent to, or blending it with, the polymeric carrier. These agents can be used alone or in combination with other suitable agents. However, there is a continual need for novel polymer coatings for use on drug delivery devices.

The embodiments described below address the above-identified needs and issues.

SUMMARY OF THE INVENTION

The present invention provides an implantable device comprising a biosoluble coating or a soluble body structure comprising a polyelectrolyte with a counterion. The polyelectrolyte and the counterion form a complex. The biosoluble body structure or biosoluble coating can completely solvate within about one month (e.g., 30 days) after deployment of the implantable device. In some embodiments, the biosoluble body structure or biosoluble coating can completely solvate within about three weeks, 15 days (e.g., two weeks), about 10 days, about one week or about 1 to 3 days after deployment of the implantable device.

If implantable device has a body structure that is not soluble, an implantable device having such a biosoluble coating deposited on a non-soluble body structure becomes a bare device (e.g., bare metal stent) after the biosoluble coating including the drugs and the coating material completely dissolves or solvates. An implantable device of the present invention therefore can avail itself of the benefits of both a coated system (e.g., drug delivery stent) and the bare metal system (e.g., bare metal stent).

In some embodiments, the biosoluble body structure or biosoluble coating can include one or more biosoluble polymer. In these embodiments, the biosoluble body structure or biosoluble coating can completely solvate or dissolve within the time frame described above.

In the case where an implantable device has a body structure that is biosoluble, the biosoluble body construct shall be formed of polymers sparingly soluble in an aqueous medium or polymers soluble in an aqueous medium but are made sparingly soluble such that implantable device (e.g., a stent) has sufficient mechanical properties to generate adequate radial force to prevent, e.g., stent movement and vascular recoil once deployed. Such an implantable device (e.g., stent) or drug delivery implantable device (e.g., a stent) would be non-thrombogenic and less inflammatory than products currently available. As used herein, the term "sparingly soluble" shall mean a solubility of lower than 1 g/L water but higher than 0.001 g/L at ambient temperature (e.g., about 20° C. or about 25° C.) and pressure (about 1 atm). In some embodiments, the term "sparingly soluble" shall mean a solubility similar to that of a soap bar or, in some other embodiments, a solubility of about 0.5 g/L or lower.

In some embodiments, the biosoluble body structure or biosoluble coating can include a bioactive agent. The bioactive agent has a release profile from the implantable device which is the same or different from the solvation or dissolution profile of the biosoluble body structure or biosoluble coating but under no circumstances would any amount of the bioactive agent remain un-released after all the matrix material dissolves or solvates. As used herein, the term "matrix material" refers to all the material of the biosoluble body structure except for the bioactive agent optionally incorporated therein or all the material of the coating except for the bioactive agent optionally incorporated therein. In some embodiments, about 80% or more of bioactive agent would release within about 1 to 3 days after deployment of an implantable device having such a biosoluble body structure or biosoluble coating.

Examples of the bioactive agent that can be included in the biosoluble coating include, but are not limited to, paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), γ-hiridun, clobetasol, pimecrolimus, imatinib mesylate, midostaurin, feno fibrate, prodrugs thereof, co-drugs thereof, and combinations thereof.

An implantable device according to the present invention can be used to treat, prevent or diagnose various conditions or disorders. Examples of such conditions or disorders include, but are not limited to, atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction and tumor obstruction. A portion of the implantable device or the whole device itself can be formed of the material, as described herein.

DETAILED DESCRIPTION

The present invention provides an implantable device comprising a biosoluble coating or a soluble body structure comprising a polyelectrolyte with a counterion. The polyelectrolyte and the counterion form a complex. The biosoluble body structure or biosoluble coating can completely solvate within about one month (e.g., 30 days) after deployment of the implantable device. In some embodiments, the biosoluble body structure or biosoluble coating can completely solvate within about three weeks, 15 days (e.g., two weeks), about 10 days, about one week or about 1 to 3 days after deployment of the implantable device.

If implantable device has a body structure that is not soluble, an implantable device having such a biosoluble coating deposited on a non-soluble body structure becomes a bare device (e.g., bare metal stent) after the biosoluble coating including the drugs and the coating material completely dissolves or solvates. An implantable device of the present invention therefore can avail itself of the benefits of both a coated system (e.g., drug delivery stent) and the bare metal system (e.g., bare metal stent).

In some embodiments, the biosoluble body structure or biosoluble coating can include one or more biosoluble polymers. In these embodiments, the biosoluble body structure or biosoluble coating can completely solvate or dissolve within the time frame described above.

In the case where an implantable device has a body structure that is biosoluble, the biosoluble body construct shall be formed of polymers sparingly soluble in an aqueous medium or polymers soluble in an aqueous medium but are made sparingly soluble such that implantable device (e.g., a stent) has sufficient mechanical properties to generate adequate radial force to prevent, e.g., stent movement and vascular recoil once deployed. Such an implantable device (e.g., stent) or drug delivery implantable device (e.g., a stent) would be non-thrombogenic and less inflammatory than products currently available. As used herein, the term "sparingly soluble" shall mean a solubility of lower than 1 g/L water but higher than 0.001 g/L at ambient temperature (e.g., about 20° C. or about 25° C.) and pressure (about 1 atm). In some embodiments, the term "sparingly soluble" shall mean a solubility similar to that of a soap bar or, in some other embodiments, a solubility of about 0.5 g/L or lower.

In some embodiments, the biosoluble body structure or biosoluble coating can include a bioactive agent. The bioactive agent has a release profile from the implantable device which is the same or different from the solvation or dissolution profile of the biosoluble body structure or biosoluble coating but under no circumstances would any amount of the bioactive agent remain un-released after all the matrix material dissolves or solvates. As used herein, the term "matrix material" refers to all the material of the biosoluble body structure except for the bioactive agent optionally incorporated therein or all the material of the coating except for the bioactive agent optionally incorporated therein. In some embodiments, about 80% or more of bioactive agent would release within about 1 to 3 days after deployment of an implantable device having such a biosoluble body structure or biosoluble coating.

As used herein, the term "completely solvates" refers to over about 99% of the material on the biosoluble coating described herein dissolves away by the physiological fluid of a body.

As used herein, the term "agent" can be used interchangeably with the term "drug".

As used herein, the term "biosoluble coating" refers to a coating that is soluble in the bloodstream and disappears as the drug releases.

As used herein, the term "not soluble" refers to body structure of or coating on an implantable device that does not completely dissolve or solvate as described above. The term "non-soluble body structure" refers to a body construct, or a portion thereof, of any non-soluble implantable device. An example of such implantable device is a stent, e.g., a bare metal stent (BMS) or polymeric stent that is fully absorbed within 2 to 3 years, which is not biosoluble as defined above.

As used herein, the term "deployment" shall mean implantation or otherwise use in a tissue of a mammal (e.g., a human such as an adult or pediatric patient or an animal) such that an implantable device is exposed to physiological fluids in the tissue. The tissue can be vessel tissue, e.g., artery or vein vessels, cardiovascular or brain vascular tissues, peripheral vessels, etc or non-vessel tissues.

Examples of the bioactive agent that can be included in the biosoluble coating include, but are not limited to, paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), γ-hiridun, clobetasol, pimecrolimus, imatinib mesylate, midostaurin, feno fibrate, prodrugs thereof, co-drugs thereof, and combinations thereof.

An implantable device according to the present invention can be used to treat, prevent or diagnose various conditions or disorders. Examples of such conditions or disorders include, but are not limited to, atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction and tumor obstruction. A portion of the implantable device or the whole device itself can be formed of the material, as described herein.

Definitions

Wherever applicable, the definitions to some terms used throughout the description of the present invention as provided below shall apply.

As used herein, the term "biostable" is used interchangeably with the term "biodurable". A biostable polymer or coating refers to a polymer or coating that is not biodegradable, which is defined blow.

The terms "biologically degradable" (or "biodegradable"), "biologically erodable" (or "bioerodable"), "biologically absorbable" (or "bioabsorbable"), and "biologically resorbable" (or "bioresorbable"), in reference to polymers and coatings, are used interchangeably and refer to polymers and coatings that are capable of being completely or substantially completely degraded, dissolved, and/or eroded over time when exposed to physiological conditions and can be gradually resorbed, absorbed and/or eliminated by the body, or that can be degraded into fragments that can pass through the kidney membrane of an animal (e.g., a human), e.g., fragments having a molecular weight of about 40,000 Daltons (40 kDa) or less. The process of breaking down and eventual absorption and elimination of the polymer or coating can be caused by, e.g., hydrolysis, metabolic processes, oxidation, enzymatic processes, bulk or surface erosion, and the like. Whenever the reference is made to "biologically degradable," "biologically erodable," "biologically absorbable," and "biologically resorbable" stent coatings or polymers forming such stent coatings, it is understood that after the process of degradation, erosion, absorption, and/or resorption has been completed or substantially completed, no coating or substantially little coating will remain on the stent. Whenever the terms "degradable," "biodegradable," or "biologically degradable" are used in this application, they are intended to broadly include biologically degradable, biologically erodable, biologically absorbable, and biologically resorbable polymers or coatings.

"Physiological conditions" refer to conditions to which an implant is exposed within the body of an animal (e.g., a human). Physiological conditions include, but are not limited to, "normal" body temperature for that species of animal (approximately 37° C. for a human) and an aqueous environment of physiologic ionic strength, pH and enzymes. In some cases, the body temperature of a particular animal may be above or below what would be considered "normal" body temperature for that species of animal. For example, the body temperature of a human may be above or below approximately 37° C. in certain cases. The scope of the present invention encompasses such cases where the physiological conditions (e.g., body temperature) of an animal are not considered "normal." A "prohealing" drug or agent, in the context of a blood-contacting implantable device, refers to a drug or agent that has the property that it promotes or enhances re-endothelialization of arterial lumen to promote healing of the vascular tissue. The portion(s) of an implantable device (e.g., a stent) containing a prohealing drug or agent can attract, bind and eventually become encapsulated by endothelial cells (e.g., endothelial progenitor cells). The attraction, binding, and encapsulation of the cells will reduce or prevent the formation of emboli or thrombi due to the loss of the mechanical properties that could occur if the stent was insufficiently encapsulated. The enhanced re-endothelialization can promote the endothelialization at a rate faster than the loss of mechanical properties of the stent.

The prohealing drug or agent can be dispersed in the body of the bioabsorbable polymer substrate or scaffolding. The prohealing drug or agent can also be dispersed within a bioabsorbable polymer coating over a surface of an implantable device (e.g., a stent).

"Endothelial progenitor cells" refer to primitive cells made in the bone marrow that can enter the bloodstream and go to areas of blood vessel injury to help repair the damage. Endothelial progenitor cells circulate in adult human peripheral blood and are mobilized from bone marrow by cytokines, growth factors, and ischemic conditions. Vascular injury is repaired by both angiogenesis and vasculogenesis mechanisms. Circulating endothelial progenitor cells contribute to repair of injured blood vessels mainly via a vasculogenesis mechanism.

As used herein, a "co-drug" is a drug that is administered concurrently or sequentially with another drug to achieve a particular pharmacological effect. The effect may be general or specific. The co-drug may exert an effect different from that of the other drug, or it may promote, enhance or potentiate the effect of the other drug.

As used herein, the term "prodrug" refers to an agent rendered less active by a chemical or biological moiety, which metabolizes into or undergoes in vivo hydrolysis to form a drug or an active ingredient thereof. The term "prodrug" can be used interchangeably with terms such as "proagent", "latentiated drugs", "bioreversible derivatives", and "congeners". N. J. Harper, Drug latentiation, *Prog Drug Res.*, 4: 221-294 (1962); E. B. Roche, Design of Biopharmaceutical Properties through Prodrugs and Analogs, Washington, D.C.: American Pharmaceutical Association (1977); A. A. Sinkula and S. H. Yalkowsky, Rationale for design of biologically reversible drug derivatives: prodrugs, *J. Pharm. Sci.*, 64: 181-210 (1975). Use of the term "prodrug" usually implies a covalent link between a drug and a chemical moiety, though some authors also use it to characterize some forms of salts of the active drug molecule. Although there is no strict universal definition of a prodrug itself, and the definition may vary from author to author, prodrugs can generally be defined as pharmacologically less active chemical derivatives that can be converted in vivo, enzymatically or nonenzymatically, to the active, or more active, drug molecules that exert a therapeutic, prophylactic or diagnostic effect. Sinkula and Yalkowsky, above; V. J. Stella et al., Prodrugs: Do they have advantages in clinical practice?, *Drugs*, 29: 455-473 (1985).

The terms "polymer" and "polymeric" refer to compounds that are the product of a polymerization reaction. These terms are inclusive of homopolymers (i.e., polymers obtained by polymerizing one type of monomer), copolymers (i.e., polymers obtained by polymerizing two or more different types of monomers), terpolymers, etc., including random, alternating, block, graft, dendritic, crosslinked and any other variations thereof.

As used herein, the term "implantable" refers to the attribute of being implantable in a mammal (e.g., a human being or patient) that meets the mechanical, physical, chemical, biological, and pharmacological requirements of a device provided by laws and regulations of a governmental agency (e.g., the U.S. FDA) such that the device is safe and effective for use as indicated by the device. As used herein, an "implantable device" may be any suitable substrate that can be implanted in a human or non-human animal. Examples of implantable devices include, but are not limited to, self-expandable stents, balloon-expandable stents, coronary stents, peripheral stents, stent-grafts, catheters, other expandable tubular devices for various bodily lumen or orifices, grafts, vascular grafts, arterio-venous grafts, by-pass grafts, pacemakers and defibrillators, leads and electrodes for the preceding, artificial heart valves, anastomotic clips, arterial closure devices, patent foramen ovale closure devices, cerebrospinal fluid shunts, and particles (e.g., drug-eluting particles, microparticles and nanoparticles). The stents may be intended for any vessel in the body, including neurological, carotid, vein graft, coronary, aortic, renal, iliac, femoral, popliteal vasculature, and urethral passages.

As used herein, the term "implantable device" is used interchangeably with the term "medical device."

An implantable device can be designed for the localized delivery of a therapeutic agent. A medicated implantable device may be constructed in part, e.g., by coating the device with a coating material containing a therapeutic agent. The body of the device may also contain a therapeutic agent.

An implantable device can be fabricated with a coating containing partially or completely a biodegradable/bioabsorbable/bioerodable polymer, a biostable polymer, or a combination thereof. An implantable device itself can also be fabricated partially or completely from a biodegradable/bioabsorbable/bioerodable polymer, a biostable polymer, or a combination thereof.

As used herein, a material that is described as a layer or a film (e.g., a coating) "disposed over" an indicated substrate (e.g., an implantable device) refers to, e.g., a coating of the material disposed directly or indirectly over at least a portion of the surface of the substrate. Direct depositing means that the coating is applied directly to the exposed surface of the substrate. Indirect depositing means that the coating is applied to an intervening layer that has been disposed directly or indirectly over the substrate. In some embodiments, the term a "layer" or a "film" excludes a film or a layer formed on a non-implantable device.

In the context of a stent, "delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

As used herein, wherein the term "water dissolvable" refers to the attribute of being water soluble of a material or polymer described in this application. This term also encompasses the attribute of a material becoming water soluble if the water includes an ion, which can be an anion, cation, or a combination in the form of a zwitterion. Examples of such ions are, but not limited to, ions present in a physiological environment, e.g., $Na^+$, $K^+$, $Ca^{+2}$, $Mg^{+2}$, $Al^{+3}$, $Cl^-$, $SO_4^{-2}$, or phosphate ions. The term "soluble" refers to the attribute of a material capable of forming a solution having a concentration of the material at least 1 g per 100 cc (or mL) of water at ambient temperature (20° C.).

As used herein, the term "slow dissolving" refers to the attribute of a polymer or material that will not completely dissolve in water or a physiological environment upon contact with water or the physiological environment but rather, will dissolve into a physiological environment over an extended period of time, e.g., one day to up to two years, e.g., a period from about 2 days to about 2 years, from about 4 days to about 20 months, from about 7 days to about 18 months, from about 14 days to about 16 months, from about 30 days to about 14 months, from about 2 months to about 12 months, or about 6 months. In some embodiments, the term "slow dissolving" can be the attribute of a polymeric matrix capable of being dissolved 50 mass % (half life) over a period up to about two years, about one year, about 6 months, about 3 moths, about 2 months, about one months, about 2 weeks, about 1 week, about 2 days, or about 1 day.

Biosoluble Polymers

Any biosoluble polymers can be used to form a coating on a stent or to provide a drug delivery particle with a bioactive agent. Examples of such polymers include, but are not limited to, poly(ethylene glycol) (PEG), poly(lactide-co-glycolide)-co-poly(ethylene glycol) (PLGA-PEG) block copolymer, other PEG copolymers, poly(vinyl alcohol) (PVA), polyvinylpyrrolidone (PVP), hyaluronic acid, hydroxyl cellulose, carboxymethylcellulose (CMC), polysaccharides, phosphoryl choline containing polymers, chitosan, collagen, and combinations thereof. In some embodiments, the biosoluble polymer can be highly crystalline, hydrophilic materials. Examples of such highly crystalline, hydrophilic materials are high molecular weight PEG or PEG based materials. As used herein, the term high molecular weight PEG generally refers to PEG having a molecular weight of about 8,000 Daltons or above, e.g., about 10K Daltons, about 15K Daltons, about 20K Daltons, about 25K Daltons, about 30K Daltons, about 35K Daltons, about 40K Daltons, about 45K Daltons, about 50K Daltons, about 55K Daltons, or about 60K Daltons or higher.

In some embodiments, the soluble polymeric matrix or coating can include a natural polymer such as chitosan, alginate, fibrin, fibrinogen, cellulose, starch, dextran, dextrin, fragments and derivatives of hyaluronic acid, heparin, fragments and derivatives of heparin, glycosamino glycan (GAG), GAG derivatives, polysaccharide, chitosan, alginate, or combinations thereof Other polymers not mentioned above that can also be used to form a coating described herein include, but are not limited to, PVP (polyvinyl pyrrolidone), polyacrylic acid, HPMC (hydroxymetheyl cellulose), gelatin, sugars and starches (such as hydroxyethyl starch and 2-O-acetyl starches), proteins, peptide polymers, mimetic peptides, silk elastin, elastin mimetic peptides, etc.

In some embodiments, where the implantable device includes a biosoluble body construct, the biosoluble body construct can include hydrophilic polymers, amphiphilic polymers, hygroscopic substances such as salts, sugar, starch, amino acids, or a composite system. The biosoluble body construct may or may not include a complex of a polyelectrolye with an counterion(s) described herein as long as the body construct is sparingly soluble or is made sparingly soluble in an aqueous medium such that an implantable device including the body construct (e.g., a stent) has sufficient mechanical properties to generate adequate radial force to prevent, e.g., stent movement and vascular recoil once deployed as described above. In some embodiments, the biosoluble body construct does not include a complex of a polyelectrolyte with a counterion(s). In other embodiments, the biosoluble body construct includes a complex of a polyelectrolyte with a counterion(s) described herein.

Polyelectrolyte

The polyelectrolyte, as used herein, are generally a polymer carrying one or more negative or positive charges. Such a polymer can form an ionic complex with one or more counterion(s).

In some embodiments, the polyelectrolyte can comprise a monomer unit that is positively or negatively charged. The polyelectrolytes used in the present invention may be copolymers that have a combination of charged and/or neutral monomers (e.g., positive and neutral; negative and neutral; positive and negative; or positive, negative and neutral). Regardless of the exact combination of charged and neutral monomers, a polyelectrolyte of the present invention is predominantly positively charged or predominantly negatively charged and hereinafter is referred to as a "positively-charged polyelectrolyte" or a "negatively-charged polyelectrolyte," respectively.

Alternatively, the polyelectrolytes can be described in terms of the average charge per repeat unit in a polymer chain. For example, a copolymer composed of 100 neutral and 300 positively charged repeat units has an average charge of 0.75 (3 out of 4 units, on average, are positively charged). As another example, a polymer that has 100 neutral, 100 negatively charged, and 300 positively charged repeat units would have an average charge of 0.4 (100 negatively charged units cancel 100 positively charged units leaving 200 positively charged units out of a total of 500 units). Thus, a positively-charged polyelectrolyte has an average charge per repeat unit between 0 and 1 and a negatively-charged polyelectrolyte has an average charge per repeat unit between 0 and −1. An example of a positively-charged copolymer is PDAD-co-PAC (i.e., poly(diallyldimethylammonium chloride) and polyacrylamide copolymer) in which the PDAD units have a charge of 1 and the PAC units are neutral so the average charge per repeat unit is less than 1.

The charges on a polyelectrolyte may be derived directly from the monomer units or they may be introduced by chemical reactions on a precursor polymer. For example, PDAD is made by polymerizing diallyldimethylammonium chloride, a positively charged water soluble vinyl monomer. PDAD-co-PAC is made by the polymerization of a mixture of diallyldimethylammonium chloride and acrylamide (a neutral monomer which remains neutral in the polymer). Poly(styrenesulfonic acid) is often made by the sulfonation of neutral polystyrene. Poly(styrenesulfonic acid) can also be made by polymerizing the negatively charged styrene sulfonate monomer. The chemical modification of precursor polymers to produce charged polymers may be incomplete and typically result in an average charge per repeat unit that is less than 1. For example, if only about 80% of the styrene repeat units of polystyrene are sulfonated, the resulting poly(styrenesulfonic acid) has an average charge per repeat unit of about –0.8.

Examples of a negatively-charged polyelectrolyte include polyelectrolytes comprising a sulfonate group ($-SO_3^-$), such as poly(styrenesulfonic acid) (PSS), poly(-acrylamido-2-methyl-1-propane sulfonic acid) (PAMPS), sulfonated poly (ether ether ketone) (SPEEK), sulfonated lignin, poly (ethylenesulfonic acid), poly(methacryloxyethylsulfonic acid), their salts, and copolymers thereof; polycarboxylates such as poly(acrylic acid) (PAA) and poly(methacrylic acid); and sulfates such as carrageenin. In some embodiments, the polyelectrolyte described herein can specifically exclude carrageenin.

Examples of a positively-charged polyelectrolyte include polyelectrolytes comprising a quaternary ammonium group, such as poly(diallyldimethylammonium chloride) (PDAD), poly(vinylbenzyltrimethylammonium) (PVBTA), ionenes, poly(acryloxyethyltrimethyl ammonium chloride), poly(methacryloxy(2-hydroxy)propyltrimethyl ammonium chloride), and copolymers thereof; polyelectrolytes comprising a pyridinium group such as poly(N-methylvinylpyridinium) (PMVP), other poly(N-alkylvinylpyridines), and copolymers thereof; and protonated polyamines such as poly(allylaminehydrochloride) (PAH) and polyethyleneimine (PEI).

Further examples of polyelectrolytes include charged biomacromolecules which are naturally occurring polyelectrolytes or their charged derivatives. A positively-charged biomacromolecule comprises a protonated sub-unit (e.g., protonated amines). Some negatively charged biomacromolecules comprise a deprotonated sub-unit (e.g., deprotonated carboxylates). Examples of biomacromolecules which may be charged for use in accordance with the present invention include proteins, polypeptides, enzymes, DNA, RNA, heparin, alginic acid, chondroitin sulfate, chitosan, chitosan sulfate, cellulose sulfate, polysaccharides, dextran sulfate and carboxymethylcellulose.

The molecular weight of synthetic polyelectrolyte molecules is typically about 1,000 to about 5,000,000 grams/mole, preferably about 10,000 to about 1,000,000 grams/mole. The molecular weight of naturally occurring polyelectrolyte molecules (i.e., biomolecules), however, can reach as high as 10,000,000 grams/mole. The polyelectrolyte typically comprises about 0.01% to about 40% by weight of a polyelectrolyte solution, and preferably about 0.1% to about 10% by weight.

Many of the foregoing polymers/polyelectrolytes, such as PDAD, exhibit some degree of branching. Branching may occur at random or at regular locations along the backbone of the polymer. Branching may also occur from a central point and in such a case the polymer is referred to as a "star" polymer, if generally linear strands of polymer emanate from the central point. If, however, branching continues to propagate away from the central point, the polymer is referred to as a "dendritic" polymer. Branched polyelectrolytes, including star polymers, comb polymers, graft polymers, and dendritic polymers, are also suitable for purposes of this invention.

In some embodiments, the polyelectrolyte can be a natural polymer carrying one or more charges. Examples of natural polyelectrolyte include, but are not limited to, chitosan, hyaluronic acid or a salt thereof, collagen, sodium alginate, carboxymethylcellulose, protein and peptide polymers if there is a counter ion (see Zhang, et al., Biomaterials, 26(16): 3353-3361(2005)).

In some embodiments, the polylyelectrolyte is soluble in water. Examples of polyelectrolytes that are soluble in water include poly(styrenesulfonic acid), poly(2-acrylamido-2-methyl-1-propane sulfonic acid), sulfonated lignin, poly(ethylenesulfonic acid), poly(methacryloxyethylsulfonic acid), poly(acrylic acids), poly(methacrylic acids) their salts, and copolymers thereof; as well as poly(diallyidimethylammonium chloride), poly(vinylbenzyltrimethylammonium), ionenes, poly(acryloxyethyltrimethyl ammonium chloride), poly(methacryloxy(2-hydroxy)propyltrimethyl ammonium chloride), and copolymers thereof; and polyelectrolytes comprising a pyridinium group, such as, poly(N-methylvinylpyridium), protonated polyamines, such as, poly(allylamine hydrochloride) and poly(ethyleneimmine). As used herein, the term "water soluble" refers to having a solubility in water of about 1 gram/100 mL water or higher.

In some embodiments, the polyelectrolyte has a limited solubility or sparing solubility in water. Examples of such polyelectrolytes include, but are not limited to, poly(N-alkylvinylpyridines), and copolymers thereof in which the alkyl group is longer than about 4 carbon atoms. Other examples of polyelectrolytes include poly(styrenesulfonic acid), poly(diallyidimethylammonium chloride), poly(N-methylvinylpyridinium) and poly(ethyleneimmine) where the small polymer counterion, such as chloride or bromide, has been replaced by a large hydrophobic counterion such as tetrabutyl ammonium, tetraethyl ammonium, iodine, hexafluorophosphate, tetrafluoroborate, or trifluoromethane sulfonate. As used herein, the term "limited solubility" shall refer to a solubility in water below 1 gram/100 mL water.

In one embodiment the negatively-charged polyelectrolyte is selected from the group consisting of poly(styrenesulfonic acid), poly(2-acrylamido-2-methyl-1-propane sulfonic acid), sulfonated lignin, poly(ethylenesulfonic acid), poly(methacryloxyethylsulfonic acid), sulfonated poly(ether ether ketone), and poly(acrylic acid). In another embodiment the positively-charged polyelectrolyte is selected from the group consisting of poly(diallyldimethylammonium chloride), poly (vinylbenzyltrimethylammonium chloride), ionenes, poly (acryloxyethyltrimethyl ammonium chloride), poly(methacryloxy(2-hydroxy)propyltrimethyl ammonium chloride), poly(N-methylvinylpyridinium), other poly (N-alkylvinyl pyridiniums), a poly(N-aryl vinyl pyridinium)and poly(allylaminehydrochloride).

Some polyelectrolytes used in accordance with the present invention generally become charged at certain pH values. For example, poly(acrylic acids) and derivatives begin to take on a negative charge within the range of about 4 to about 6 and are negatively charged at higher pH levels. Below this transition pH range, however, poly(acrylic acids) are protonated (i.e., uncharged). Similarly, polyamines and derivative thereof take on a positive charge if the pH of the solution is below about 8. As such, and in accordance with the present invention, the pH of a polyelectrolyte solution may be adjusted by the addition of an acid and/or base in order to attain, maintain, and/or adjust the electrical charge of a polyelectrolyte.

The term "counterion", as used herein, refers to an ionic moiety that carries a charge(s) opposite to the charge on the polyelectrolyte. The counterion is capable of forming a complex with the polyelectrolyte. A complex formed by the polyelectrolyte and the counterion can have ionic bonding or chemical bonding (e.g., co-valent bonding) between the polyelectrolyte and the counterion. Generally, ionic bonding can form when both the polyelectrolyte and the counterion(s) are present in, e.g., an aqueous or nonaqueous solution. Chemical bonding such as co-valent bonding between the counterion and the polyelectrolyte can also form via a chemical reaction between the counterion and the polyelectrolyte, which sometimes can occur via the co-presence of the counterion and the polyelectrolyte in a solution or, in some embodiments, can be caused to occur with certain conditions, e.g., pH, temperature, or pressure, that an ordinary skill in the art can determine according to documented methodology or process.

The counterion can be hydrophilic or hydrophobic, depending on the nature of the polyelectrolyte and the need for modulation of the solubility of a coating comprising the complex for controlled release of an optional drug in the coating. For example, if the polyelectrolyte is hydrophilic and fast dissolving, to modulate the solubility of a coating comprising a complex formed of the polyelectrolyte, the complex may need to include a counterion that is hydrophobic or more hydrophobic than the polyelectrolyte such that the complex can dissolve in a physiologic environment slower so as to provide a controlled release of an optional drug that may be included in a coating comprising the complex. Alternatively, if the polyelectrolyte is hydrophobic and slow dissolving, to modulate the solubility of a coating comprising a complex formed of the polyelectrolyte, the complex may need to include a counterion that is hydrophilic or more hydrophilic than the polyelectrolyte such that the complex can dissolve in a physiologic environment faster so as to provide a controlled release of an optional drug that may be included in a coating comprising the complex.

Examples of hydrophobic counterions include, but are not limited to:
cationic tetradecyldimethylhydroxylammonium chloride,
p-propyibenzenesulfonate ions,
(poly(styrene)-co-styrene sulphonate,
tetrabutylammoniumhydroxide,
tetraisobutylammoniumhydroxide,
lauryl acid,
stearyl acid,
nonyl acid, and
alkyltrimethylammonium or tetraalkylammonium, etc.

A preferred hydrophobic counterion for forming a complex with a polyelectrolyte is a high pKa counterion. As used herein, the term "high pKa" refers to a counterion capable of forming a complex with a chosen polyelectrolyte, the complex capable of dissociation back to the counterion and the polyelectrolyte with a thermodynamic dissociation constant pKa of about −3.5 or higher, of about 2 or higher, or about −1 or higher.

Examples of hydrophilic counterions include, but are not limited to, water soluble organic or inorganic ions, e.g., $Cl^-$, $Br^-$, $I^-$, $SO_4^{-2}$, $CO_3^{-2}$, $-COO^-$, $HCO_3^-$, $Na^+$, $K^+$, $NH_4^+$, $H^+$, $Ca^{2+}$, $Mg^{+2}$, $Al^{+3}$, or phosphate ions such as $PO_4^{-3}$ or $HPO_4^{-2}$, etc. In some embodiments, a hydrophilic coutnerion can also include or be attached to a hydrophilic group or linkage, examples of which include poly(ethylene glycol) (PEG), polyalkylene oxide (e.g., polyethylene oxide).

In some embodiments, the counterion can be an oppositely charged polyelectrolyte. In these embodiments, the two or more oppositely charged polyelectrolytes formed a complex comprising these two or more oppositely charged polyelectrolytes.

Bioactive Agents

These bioactive agents can be any agent which is a therapeutic, prophylactic, or diagnostic agent. These agents can have anti-proliferative or anti-inflammatory properties or can have other properties such as antineoplastic, antiplatelet, anticoagulant, anti-fibrin, antithrombonic, antimitotic, antibiotic, antiallergic, or antioxidant properties.

These agents can be cystostatic agents, agents that promote the healing of the endothelium (other than by releasing or generating NO), or agents that promote the attachment, migration and proliferation of endothelial cells while quenching smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules, which bind to complementary DNA to inhibit transcription, and ribozymes. Some other examples of bioactive agents include antibodies, receptor ligands, enzymes, adhesion peptides, blood clotting factors, inhibitors or clot dissolving agents, such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include ABT-578, 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include biolimus, tacrolimus, dexamethasone, clobetasol, corticosteroids or combinations thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, and genetically engineered epithelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable.

In some embodiments, the bioactive agent that can be included in a coating described herein can specifically exclude any one or more of the above identified drugs or agents.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient, the nature of the trauma, the nature of the therapy desired, the time over which the ingredient administered resides at the vascular site, and if other active agents are employed, the nature and type of the substance or combination of substances. Therapeutically effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by those of ordinary skill in the art.

Coating Construct

According to some embodiments of the invention, optionally in combination with one or more other embodiments described herein, a coating disposed over an implantable device (e.g., a stent) can include a complex of a polyelectrolyte and a counterion(s) described herein in a layer according to any design of a coating. The coating can be a multi-layer structure that includes at least one reservoir layer, which is layer (2) described below, and can include any of the following (1), (3), (4) and (5) layers or combination thereof:
 (1) a primer layer; (optional);
 (2) a reservoir layer (also referred to "matrix layer" or "drug matrix"), which can be a drug-polyelectrolyte layer including at least one polymer (drug- polyelectrolyte layer) or, alternatively, a polymer-free drug layer;
 (3) a release control layer (also referred to as a "rate-limiting layer") (optional);
 (4) a topcoat layer; and/or (optional); and
 (5) a finishing coat layer (optional).

In some embodiments, a coating of the invention can include two or more reservoir layers described above, each of which can include a bioactive agent described herein.

Each layer of a stent coating can be disposed over the implantable device (e.g., a stent) by dissolving the complex of a polyelectrolyte and a counterion(s), optionally with one or more other polymers, in a solvent, or a mixture of solvents, and disposing the resulting coating solution over the stent by spraying or immersing the stent in the solution. After the solution has been disposed over the stent, the coating is dried by allowing the solvent to evaporate. The process of drying can be accelerated if the drying is conducted at an elevated temperature. The complete stent coating can be optionally annealed at a temperature between about 40° C. and about 150° C., e.g., 80° C., for a period of time between about 5 minutes and about 60 minutes, if desired, to allow for crystallization of the coating, and/or to improve the thermodynamic stability of the coating.

To incorporate a bioactive agent (e.g., a drug) into the reservoir layer, the drug can be combined with the coating solution that is disposed over the implantable device as described above. Alternatively, if it is desirable a polymer-free reservoir can be made. To fabricate a polymer-free reservoir, the drug can be dissolved in a suitable solvent or mixture of solvents, and the resulting drug solution can be disposed over the implantable device (e.g., stent) by spraying or immersing the stent in the drug-containing solution.

Instead of introducing a drug via a solution, the drug can be introduced as a colloid system, such as a suspension in an appropriate solvent phase. To make the suspension, the drug can be dispersed in the solvent phase using conventional techniques used in colloid chemistry. Depending on a variety of factors, e.g., the nature of the drug, those having ordinary skill in the art can select the solvent to form the solvent phase of the suspension, as well as the quantity of the drug to be dispersed in the solvent phase. Optionally, a surfactant can be added to stabilize the suspension. The suspension can be mixed with a coating solution and the mixture can be disposed over the stent as described above. Alternatively, the drug suspension can be disposed over the stent without being mixed with the coating solution.

The drug-polyelectrolyte layer can be applied directly or indirectly over at least a portion of the stent surface to serve as a reservoir for at least one bioactive agent (e.g., drug) that is incorporated into the reservoir layer. The optional primer layer can be applied between the stent and the reservoir to improve the adhesion of the drug-polyelectrolyte layer to the stent. The optional topcoat layer can be applied over at least a portion of the reservoir layer and serves as a rate-limiting membrane that helps to control the rate of release of the drug. In one embodiment, the topcoat layer can be essentially free from any bioactive agents or drugs. If the topcoat layer is used, the optional finishing coat layer can be applied over at least a portion of the topcoat layer for further control of the drug-release rate and for improving the biocompatibility of the coating. Without the topcoat layer, the finishing coat layer can be deposited directly on the reservoir layer.

Sterilization of a coated medical device generally involves a process for inactivation of micropathogens. Such processes are well known in the art. A few examples are e-beam, ETO sterilization, and irradiation. Most, if not all, of these processes can involve an elevated temperature. For example, ETO sterilization of a coated stent generally involves heating above 50° C. at humidity levels reaching up to 100% for periods of a few hours up to 24 hours. A typical EtO cycle would have the temperature in the enclosed chamber to reach as high as above 50° C. within the first 3-4 hours then and fluctuate between 40° C. to 50° C. for 17-18 hours while the humidity would reach the peak at 100% and maintain above 80% during the fluctuation time of the cycle.

The process of the release of a drug from a coating having both topcoat and finishing coat layers includes at least three steps. First, the drug is absorbed by the polymer of the topcoat layer at the drug-polyelectrolyte layer/topcoat layer interface. Next, the drug diffuses through the topcoat layer using the void volume between the macromolecules of the topcoat layer polymer as pathways for migration. Next, the drug arrives at the topcoat layer/finishing layer interface. Finally, the drug diffuses through the finishing coat layer in a similar fashion, arrives at the outer surface of the finishing coat layer, and desorbs from the outer surface. At this point, the drug is released into the blood vessel or surrounding tissue. Consequently, a combination of the topcoat and finishing coat layers, if used, can serve as a rate-limiting barrier. The drug can be released by virtue of the degradation, dissolution, and/or erosion of the layer(s) forming the coating, or via migration of the drug through the layer(s) of coating into a blood vessel or tissue.

In one embodiment, any or all of the layers of the stent coating can be made of a complex of a polyelectrolyte and a counterion(s) described herein, optionally having the properties of being biologically degradable/erodable/absorbable/resorbable, non-degradable/biostable polymer, or a combination thereof. In another embodiment, the outermost layer of the coating can be limited to a complex of a polyelectrolyte and a counterion(s) as defined above.

To illustrate in more detail, in a stent coating having all four layers described above (i.e., the primer, the reservoir layer, the topcoat layer and the finishing coat layer), the outermost layer is the finishing coat layer, which can be made of a complex of a polyelectrolyte and a counterion(s) described herein. The remaining layers (i.e., the primer, the reservoir layer and the topcoat layer) optionally having the properties of being biosoluble. The polymer(s) in a particular layer may be the same as or different than those in any of the other layers, as long as they are biosoluble within the time frame described above. As another illustration, the coating can include a single matrix layer comprising a polymer described herein and a drug.

If a finishing coat layer is not used, the topcoat layer can be the outermost layer and should be made of a complex of a polyelectrolyte and a counterion(s) described herein. In this case, the remaining layers (i.e., the primer and the reservoir layer) optionally can also be fabricated of a complex of a polyelectrolyte and a counterion(s) described herein and optionally having the properties of being biosoluble. The polymer(s) in a particular layer may be the same as or different than those in any of the other layers, as long as they are biosoluble within the time frame described above.

If neither a finishing coat layer nor a topcoat layer is used, the stent coating could have only two layers—the primer and the reservoir. In such a case, the reservoir is the outermost layer of the stent coating and should be made of a complex of a polyelectrolyte and a counterion(s) described herein. The primer optionally can also be fabricated of a complex of a polyelectrolyte and a counterion(s) described herein. The two layers may be made from the same or different polymers, as long as they are biosoluble within the time frame described above.

Any layer of a coating can contain any amount of a complex of a polyelectrolyte and a counterion(s) described herein and optionally being mixed with a biosoluble polymer, which is described above, other than the complex of a polyelectrolyte and a counterion.

Method of Fabricating A Device

The coating described herein can be formed by spray coating or any other coating process available in the art. Generally, the coating involves dissolving or suspending the composition, or one or more components thereof, in a solvent or solvent mixture to form a solution, suspension, or dispersion of the composition or one or more components thereof, applying the solution or suspension to an implantable device, and removing the solvent or solvent mixture to form a coating or a layer of coating. Suspensions or dispersions of the composition described herein can be in the form of latex or emulsion of microparticles having a size between 1 nanometer and 100 microns, preferably between 1 nanometer and 10 microns. Heat and/or pressure treatment can be applied to any of the steps involved herein. In addition, if desirable, the coating described here can be subjected to further heat and/or pressure treatment. Some additional exemplary processes of coating an implantable device that may be used are described in, for example, Lambert T L, et al. Circulation, 1994, 90: 1003-1011; Hwang C W, et al. Circulation, 2001, 104: 600-605; Van der Giessen W J, et al. Circulation, 1996, 94: 1690-1697; Lincoff A M, et al. J Am Coll Cardiol 1997, 29: 808-816; Grube E. et al, J American College Cardiology Meeting, Mar. 6, 2002, ACCIS2002, poster 1174-15; Grube E, et al, Circulation, 2003, 107: 1, 38-42; Bullesfeld L, et al. Z Kardiol, 2003, 92: 10, 825-832; and Tanabe K, et al. Circulation 2003, 107: 4, 559-64.

Other embodiments of the invention, optionally in combination with one or more other embodiments described herein, are drawn to a method of fabricating an implantable device comprising a biosoluble structure.

In some embodiments, to form an implantable device formed from a polymer, a polymer or copolymer optionally including at least one bioactive agent described herein can be formed into a polymer construct, such as a tube or sheet that can be rolled or bonded to form a construct such as a tube. An implantable device can then be fabricated from the construct. For example, a stent can be fabricated from a tube by laser machining a pattern into the tube. In another embodiment, a polymer construct can be formed from the polymeric material of the invention using an injection-molding apparatus. In these embodiments, a bioactive agent can be incorporated into the device by conventional spray coating techniques or by incorporating the bioactive agent into soluble polymer construct such that the bioactive agent is part of the biosoluble construct if the method of making the implantable device is fashioned in a multilayer technique such as co-extrusion.

As used herein, the term "solvent" refers to a liquid substance or composition that is compatible with the polymer and is capable of dissolving or suspending the polymeric composition or one or more components thereof at a desired concentration. Representative examples of solvents include chloroform, acetone, water (buffered saline), dimethylsulfoxide (DMSO), propylene glycol monomethyl ether (PM,) isopropylalcohol (IPA), n-propyl alcohol, methanol, ethanol, tetrahydrofuran (THF), dimethylformamide (DMF), dimethyl acetamide (DMAC), benzene, toluene, xylene, hexane, cyclohexane, heptane, octane, nonane, decane, decalin, ethyl acetate, butyl acetate, isobutyl acetate, isopropyl acetate, butanol, diacetone alcohol, benzyl alcohol, 2-butanone, cyclohexanone, dioxane, methylene chloride, carbon tetrachloride, tetrachloroethylene, tetrachloro ethane, chlorobenzene, 1,1,1-trichloroethane, 1,1,2-trichloroethane, formamide, hexafluoroisopropanol, 1,1,1-trifluoroethanol, and hexamethyl phosphoramide and a combination thereof.

Examples of such implantable devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP2ON," ELASTINITE (Nitinol), tantalum, nickel-titanium alloy, platinum-iridium alloy, gold, magnesium, or combinations thereof. "MP35N" and "MP2ON" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP2ON" consists of 50% cobalt, 20% nickel, 20% chromium, and 10% molybdenum. Devices made from bioabsorbable or biostable polymers could also be used with the embodiments of the present invention. In one embodiment, the implantable device is a stent, which can be degradable stents, biodurable stents, depot stents, and metallic stens such as stents made of stainless steel or nitinol. The stents can be balloon expandable or self expanding.

Method of Treating or Preventing Disorders

An implantable device according to the present invention can be used to treat, prevent or diagnose various conditions or disorders. Examples of such conditions or disorders include, but are not limited to, atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction and tumor obstruction.

In certain embodiments, optionally in combination with one or more other embodiments described herein, the inventive method treats, prevents or diagnoses a condition or disorder selected from atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, arteriovenous anastamoses, bile duct obstruction, ureter obstruction and tumor obstruction. In a particular embodiment, the condition or disorder is atherosclerosis, thrombosis, restenosis or vulnerable plaque.

In one embodiment of the method, optionally in combination with one or more other embodiments described herein, the implantable device can include at least one biologically active agent that is not an anti-proliferative agent or an anti-inflammatory agent. Examples of such agents are described above, which include, but are not limited to, nitric oxide donors, super oxide dismutases, super oxide dismutase mimics, 4-amino-2,2,6,6-tetramethylpiperidine-1-oxyl (4-amino-TEMPO), imatinib mesylate, estradiol, progenitor cell-capturing antibodies, prohealing drugs, prodrugs thereof, co-drugs thereof, and a combination thereof.

In certain embodiments, optionally in combination with one or more other embodiments described herein, the implantable device used in the method is selected from stents, grafts, stent-grafts, catheters, leads and electrodes, clips, shunts, closure devices, valves, and particles. In a specific embodiment, the implantable device is a stent.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

The invention claimed is:

1. An implantable device comprising a biosoluble body structure and optionally comprising a coating deposited on the body structure of the implantable device, the biosoluble body structure comprising:
a complex comprising a polyelectrolyte and a counterion, the polyelectrolyte being poly(2-acrylamido-2-methyl-1-propane sulfonic acid) (PAMPS), sulfonated poly(ether ether ketone) (SPEEK), poly(acryloxyethyltrimethyl ammonium chloride), poly(methacryloxy(2-hydroxy)propyltrimethyl ammonium chloride), or a combination thereof; wherein the implantable device is selected from the group consisting of stents, stent-grafts, catheters, grafts, pacemakers, defibrillators, leads for pacemakers, leads for defibrillators, electrodes for pacemakers, electrodes for defibrillators, artificial heart valves, anastomotic clips, arterial closure devices, patent foramen ovale closure devices, and cerebrospinal fluid shunts.

2. The implantable device of claim 1, wherein the biosoluble body structure further comprises a bioactive agent.

3. The implantable device of claim 1, wherein the counterion is a hydrophobic counterion.

4. The implantable device of claim 1, wherein the complex has a high dissociation constant (pKa).

5. The implantable device of claim 2, wherein the bioactive agent is selected from the group consisting of paclitaxel, docetaxel, estradiol, 17-beta-estradiol, nitric oxide donors, super oxide dismutases, 4-amino-2,2,6,6-tetramethylpiperidine-1-oxyl (4-amino-TEMPO), biolimus, tacrolimus, dexamethasone, rapamycin, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578 ), γ-hiridun, clobetasol, pimecrolimus, imatinib mesylate, midostaurin, fenofibrate, and combinations thereof.

6. The implantable device of claim 1, wherein the optional coating is present.

7. The implantable device of claim 1, wherein the biosoluble body structure further comprises a biosoluble polymer selected from the group consisting of poly(ethylene glycol) (PEG), poly(lactide-co-glycolide)-co-poly(ethylene glycol) (PLGA-PEG) block copolymers, other PEG copolymers, poly(vinyl alcohol) (PVA), hyaluronic acid, hydroxyl cellulose, Carboxymethylcellulose (CMC), polysaccharides, phosphoryl choline containing polymers, chitosan, collagen, and combinations thereof.

8. The implantable device of claim 2, wherein the bioactive agent is selected from the group consisting of paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578 ), γ-hiridun, clobetasol, pimecrolimus, imatinib mesylate, midostaurin, fenofibrate, and combinations thereof.

9. The implantable device of claim 1, wherein the body structure of the implantable device is a.

10. The implantable device of claim 1,
wherein the polyelectrolyte is poly(2-acrylamido-2-methyl-1-propane sulfonic acid) (PAMPS), sulfonated poly(ether ether ketone) (SPEEK), or a combination thereof.

11. The implantable device of claim 1, wherein the polyelectrolyte is poly(acryloxyethyltrimethyl ammonium chloride), poly(methacryloxy(2-hydroxy) -propyltrimethyl ammonium chloride), or a combination thereof.

12. A method of fabricating an implantable device, comprising
forming a biosoluble body structure comprising:
a complex comprising a polyelectrolyte and a counterion, the polyelectrolyte being poly(2-acrylamido-2-methyl-1-propane sulfonic acid) (PAMPS), sulfonated poly(ether ether ketone) (SPEEK), poly(acryloxyethyltrimethyl ammonium chloride), poly(methacryloxy(2-hydroxy)propyltrimethyl ammonium chloride, or a combination thereof; wherein the implantable device is selected from the group consisting of stents, stent-grafts, catheters, grafts, pacemakers, defibrillators, leads for pacemakers, leads for defibrillators, electrodes for pacemakers, electrodes for defibrillators, artificial heart valves, anastomotic clips, arterial closure devices, patent foramen ovale closure devices, and cerebrospinal fluid shunts.

13. The method of claim 12, wherein the implantable device further comprises a bioactive agent.

14. The method of claim 12, wherein the counterion is a hydrophobic counterion.

15. The method of claim 12, wherein the complex has a high dissociation constant (pKa).

16. The method of claim 13, wherein the bioactive agent is selected from the group consisting of paclitaxel, docetaxel, estradiol, 17-beta-estradiol, nitric oxide donors, super oxide dismutases, 4-amino-2,2,6,6-tetramethylpiperidine-1-oxyl (4-amino-TEMPO), biolimus, tacrolimus, dexamethasone, rapamycin, 40-O-(2-hydroxy)ethyl-rapamycin (everolimus), 40-O-(3-hydroxy)propyl-rapamycin, 40 -O-[(2-hydroxy)ethoxy ]ethyl-rapamycin, 40-O-tetrazole-rapamycin, 40-epi-(N1-tetrazolyl)-rapamycin (ABT-578 ), γ-hiridun, clobetasol, pimecrolimus, imatinib mesylate, midostaurin, fenofibrate, and combinations thereof.

17. The method of claim 12, further comprising depositing a coating on the biosoluble body structure.

18. The method of claim 12, wherein the biosoluble body structure is a stent.

19. The method of claim 12, wherein the biosoluble body structure further comprises a biosoluble polymer selected from the group consisting of poly(ethylene glycol) (PEG), poly(lactide-co-glycolide)-co-poly(ethylene glycol) (PLGA-PEG) block copolymers, other PEG copolymers, poly(vinyl alcohol) (PVA), hyaluronic acid, hydroxyl cellulose, Carboxymethylcellulose (CMC), polysaccharides, phosphoryl choline containing polymers, chitosan, collagen, and combinations thereof.

20. The method of claim 13, wherein the bioactive agent is selected from the group consisting of paclitaxel, docetaxel, estradiol, 17-beta-estradiol, nitric oxide donors, super oxide dismutases, super oxide dismutases mimics, 4-amino-2,2,6,6-tetramethylpiperidine-1-oxyl (4-amino-TEMPO), biolimus, tacrolimus, dexamethasone, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578 ), γ-hiridun, clobetasol, pimecrolimus, imatinib mesylate, midostaurin, fenofibrate, and combinations thereof.

* * * * *